United States Patent [19]

Srebnik et al.

[11] Patent Number: 5,468,889
[45] Date of Patent: Nov. 21, 1995

[54] BORYL ZIRCONOCENE ORGANIC 1,1-DIMETALLIC COMPOUNDS

[75] Inventors: Morris Srebnik, Sylvania; Bin Zheng; Laurent Deloux, both of Toledo, all of Ohio

[73] Assignee: The University of Toledo, Toledo, Ohio

[21] Appl. No.: 261,780

[22] Filed: Jun. 20, 1994

[51] Int. Cl.$^6$ .............................. C07F 7/00; C07F 17/00; C07F 5/02

[52] U.S. Cl. ........................... 556/7; 556/53; 556/56

[58] Field of Search .................... 556/7, 53, 56

[56] References Cited

PUBLICATIONS

Skrzypczak–Jankum et al., J. Chem. Soc., Chem. Commun., No. 2, pp. 127–128 (21 Jan. 1994).
Zheng et al., Tetrahedron Letters, vol. 34, No. 26, pp. 4133–4136 (1993).

*Primary Examiner*—Porfirio Nazario-Gonzalez
*Attorney, Agent, or Firm*—Marshall & Melhorn

[57] ABSTRACT

Boron-zirconium 1,1,-dimetallic organic compounds useful in organic synthesis such as the preparation of alpha-bromoboranes. The boron-zirconium compounds include boron and zirconiun, and in particular the synthesis, structure and reactivity of E-chlorobis(cyclopentadienyl)- [1-(4,4,5,5-tetramethyl-1,3,2-dioxaborolane-2-yl)-3,3-dimethylbutenyl] zirconium(IV).

19 Claims, No Drawings

BORYL ZIRCONOCENE ORGANIC 1,1-DIMETALLIC COMPOUNDS

The present invention relates to boryl zirconocene dimetallic compounds such as chlorobis(cyclopentadienyl) [1-(1,3,2-dioxaborinane-2-yl)hexyl]zirconium(IV).

BACKGROUND OF THE INVENTION

There has been growing interest in the synthesis or organozirconium compounds owing to recent reports of their applications in bond-breaking reactions, insertion reactions, conjugate additions, olefin cross-coupling reactions, Grignard-type additions, and especially in their potential applications as catalysts for stereo- or regio-selective polymerizations of olefins.

1,1-Bimetallics of transition metals are well-known to serve a wide range of applications towards organic synthesis. However, the chemistry of 1,1-bimetallics containing zirconium has not been extensively studied, and only a few cases have been reported, including zirconium with zinc as well as aluminum. The examples of the use of boron in organic synthesis are legion. In order to extend organozirconiumboron chemistry, it would be of great value to develop a novel class of 1,1-bimetallics based on zirconium and boron. Since both zirconium and boron are lewis acids, it is reasonable to expect that zirconium and boron bimetallics could be potentially applied in organic synthesis as stoichiometric reagents and in polymerization of olefins as Lewis acid catalysts.

Thus, hydrozirconation is one of the most promising organometallic techniques used in organic synthesis. Schwartz and co-workers have developed this reaction in a series of papers as follows:

1. Schwartz, J.; Hart, D. W. *J. Am. Chem. Soc.* 1974, 96, 8115.
2. Schwartz, J.; Labinger, J. A. *Angew. Chem. Int. Ed. Engl.* 1976, 15, 333.
3. Hart, D. W.; Blackburn, T. F.; Schwartz, J. *J. Am. Chem. Soc.* 1975, 97, 680.
4. Bertelo, C. A.; Schwartz, J. *J. Am. Chem. Soc.* 1976, 98, 262.
5. Carr, D. B.; Schwartz, J. *J. Am. Chem. Soc.* 1979, 101, 3521.

It would be desirable to provide new bimetallic compounds containing Zr and B that provide superior and unexpected organic synthesis products and are useful as effective catalysts for the polymerization of alpha-olefins.

OBJECTS OF THE INVENTION

It is an object of the present invention to provide an organic bimetallic compound containing Zr and B in which Cp is bis(cyclopentadienyl), the compound having the following structure:

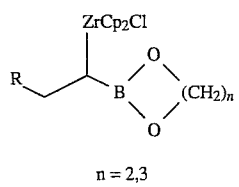

n = 2,3

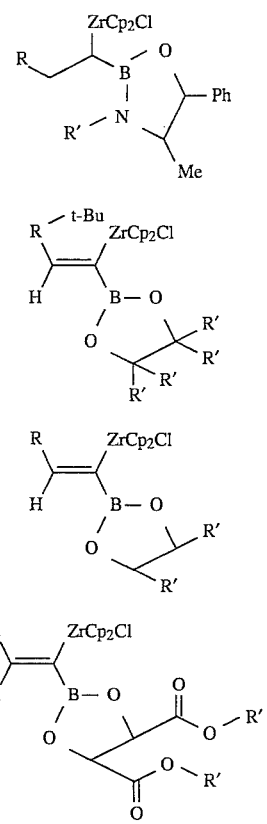

where R is an organic radical having 2 to 20 carbon atoms that is aliphatic, aromatic, heteroaromatic, or cyclic, or their halogenated substituted derivatives; and where R is an alkyl group of 1 to 8 carbon atoms.

It is an object of the present invention to provide a 1,1-bimetallic compound having the following formula:

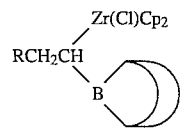

, where R is an alkyl, except tert-butyl, alkenyl, cycloalkyl, phenyl, alkylphenyl and their chloro- or bromo-substituted derivatives; where

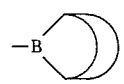

is B-borabicyclo [3.3.1]nonyl, and where $Cp_2$ is bis (cyclopentadienyl).

It is an object of the present invention to provide an optically inactive compound having the structure:

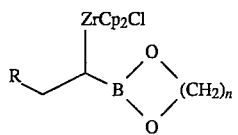

It is an object of the present invention to provide an optically active compound having the structure:

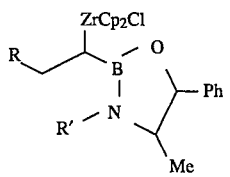

These and other objects will be apparent from the specification and the appended claims.

SUMMARY OF THE INVENTION

The present invention provides an organic bimetallic compound containing Zr and B in which Cp is bis (cyclopentadienyl), the compound having the following structure:

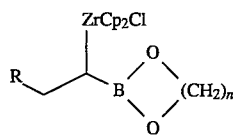

n = 2,3

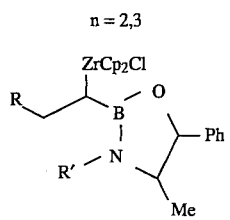

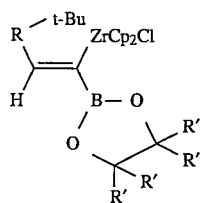

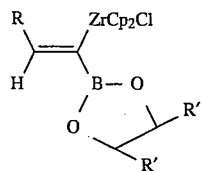

where R is an organic radical having 2 to 20 carbon atoms that is aliphatic, aromatic, heteroaromatic, or cyclic, or their halogenated substituted derivatives where $R^1$ is an alkyl group of 1 to 8 carbon atoms.

The present invention also provides a 1,1-bimetallic compound having the following formula:

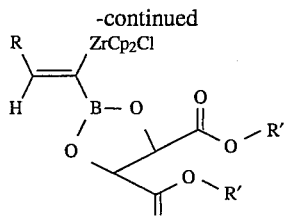

, where R is an alkyl, except tert-butyl, alkenyl, cycloalkyl, phenyl, alkylphenyl and their chloro- or bromo-substituted derivatives; where

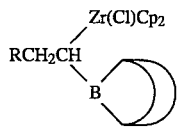

is B-borabicyclo[3.3.1]nonyl, and where Cp is bis(cyclopentadienyl).

DETAILED DESCRIPTION OF THE INVENTION

The 1,1-dimetallic compounds (containing Zr and B) of the present invention are useful in organic synthesis to produce organic products, the synthesis utilizing the reactivity of the zirconium-carbon bond with electrophilic reagents.

The following example illustrates the preparation of the boron-zirconium 1,1-bimetallic compounds of the invention and their use in preparing alpha-bromoboranes.

Example 1

It has been found that hydrozirconation of various B-alkenyl borabicyclo[3.3.1]nonanes 1 (B-alkenyl-9-BBN) by Schwartz's reagent, $H(Cl)ZrCp_2$ proceeds smoothly in dichloromethane providing 1,1-bimetallics of boron and zirconium depicted as 2 (eq 1).

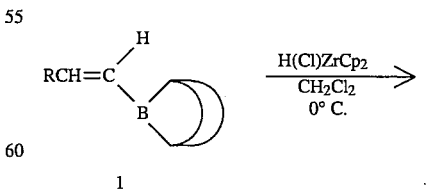

1

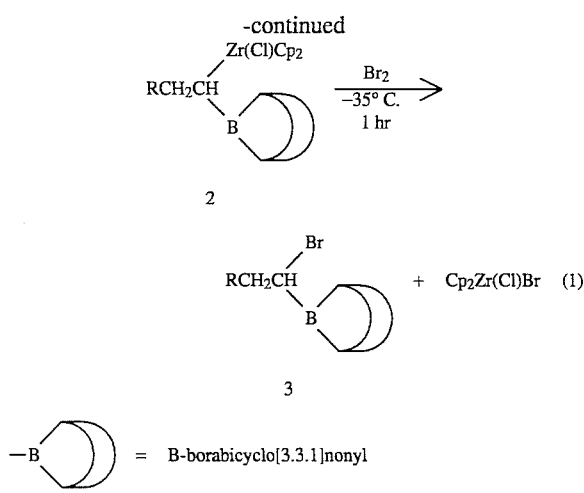

and THF are suitable solvents.

We have also found that cyclic alkenylboronic esters, such as hexenyl-1,3,2-benzodioxaborole, ethylene glycol hexenylboronate and pinacol hexenylboronate, underwent partial hydrozirconation with one equivalent of Schwartz's reagent slowly. Alternatively, groups substituted on boron atom larger than 9-BBN also inhibited the rate of hydrozirconation. Thus diisopinocamphenyl hexenylborane and diisocaranyl hexenylborane were incompletely hydrozirconated at reduced rate. Obviously both electronic and steric factors greatly influence the course of hydrozirconation of B-alkenylboranes.

Addition of bromine in dichloromethane in situ at −35° C. resulted in the immediate discharge of color and yielded the slow formation of a white precipitate within 1 hour. The proton NMR of this isolated solid material is consistent with a zirconocene dihalide. After pumping off dichloromethane, extraction with hexanes from the reaction mixture provided the crude oily alpha-bromoboranes in high yields. The results are summarized in Table I. This reaction serves two

TABLE I

Preparation of α-Bromoboranes 3 by Bromination of 1,1-bimetallic compounds 2.

| Entry | R in Vinyl-9-BBN, 1 | Hydrozirconation Time, hr | Bromination Product, 3 | $^1$H NMR δ (ppm) of α-H(dd) | Yield[a] % |
|---|---|---|---|---|---|
| 1 | n-butyl | 1 | | 4.13 | 97 |
| 2 | 3-chloropropyl | 1 | | 4.08 | 99 |
| 3 | 1-methylpropyl | 1.5 | | 4.10 | 95 |
| 4 | 3-phenylpropyl | 1.5 | | 4.26 | 99 |
| 5 | cyclopentyl | 2 | | 4.19 | 91 |
| 6 | t-butyl | 6 | | 4.24 | 87 |
| 7 | phenyl | 6 | | 4.27 | 83 |

[a]crude yields, percent based on vinyl-9-BBN

Hydrozirconation was completed in dichloromethane and THF, and took 1 hour and 1.5 hours respectively at 0° C. for B-hexenyl-9-BBN. The study of solvent effect suggested that the electronic donor ability of a solvent favors the hydrozirconation process. This is different from the solvent effect observed in hydroboration where both diethyl ether purposes. It provides confirmation of the regioselectivity of the hydrozirconation step, and secondly generates the useful alpha-bromoboranes which can be converted into a multitude of organic products conveniently.

In addition to these results, the hydrozirconation of B-(-3-methoxy-1-propenyl)-9-BBN was carried out. By comparison with B-hexenyl-9-BBN, the required time for hydrozirconation was shortened by half. This interesting result hints that the coordination of zirconium in Schwartz's reagent to electronegative atom, oxygen, in the alkenylboranes speeds up the hydrozirconation.

The formed dimetallics and the product of bromination were complex.

In conclusion, 1,1-bimetalloalkanes of zirconium and boron were prepared by hydrozirconation of alkenylboranes with Schwartz's reagent. A selective cleavage of carbon-zirconium bond in these 1,1-bimetallics provides a convenient method to obtain alpha-bromoboranes.

Example 2

This illustrates the typical procedure for preparation of B-(-1-bromohexyl)-9borabicyclo[3.3.1]nonane: All reactions and operations were under argon. To a stirred ice-cooled suspension of Schwartz's reagent (0.26g, 1 mmol) in dry $CH_2Cl_2$ (1 ml) was added a solution of B-hexenyl-9-BBN (0.20 g, 1 mmol) in dry $CH_2Cl_2$ (1 ml). The cloudy suspension of the mixture become clear yellow solution in 1 hour at 0° C. (or 10 minutes at ambient temperature). After cooling to −35° C., bromine (0.16 g, 1 mmol) in 1 ml of $CH_2Cl_2$ was added dropwise. As the reaction mixture become colorless, a white precipitate slowly formed. The resulting mixture was stirred 1 hour, and warmed to ambient temperature. After pumping off $CH_2Cl_2$, dry hexanes (2×2ml) was added, and the reaction mixture extracted. Filtration of this hexanes solution and evaporation of the solvent from the filtrate afforded the crude product, alpha-bromohexyl-9-BBN, as a clear colorless oil (0.27g, 97%). Organic products were identified by $^1$H NMR.

Example 3

Recently, we synthesized a series of boron-zirconium 1,1-dimetalloalkanes and showed that they undergo selective cleavage of the carbon-zirconium bond with a series of electrophiles. In this communication we describe the preparation of 1,1-dimetalloalkenes based on boron and zirconiun, and in particular the synthesis, structure and reactivity of E-chlorobis(cyclopentadienyl)- [1-(4,4,5,5-tetramethyl-1,3,2-dioxaborolane-2-yl)-3,3- dimethylbutenyl]zirconium(IV) (2) which to our knowledge is the first example of this new class of 1,1-dimetalloalkenes.

The synthesis of (2) is outlined in Scheme I. 2-(3,3-dimethylbutynyl)-4,4,5,5-tetramethyl-1,3,2-dioxaborolane (1) was prepared in high yield according to the method of Bhat et al. from the reaction of 1-lithio-3,3-dimethyl-1-butyne with 2-isopropoxy-4,4,5,5 ,- tetramethyl-1,3,2-dioxaborolane at −78° C., followed by treatment with ethereal hydrogen chloride. Hydrozirconation of (1) with 1.2 equiv of zirconocene hydrochloride afforded the desired product (81.5% isolated yield) as a pale greenish crystalline solid.

Scheme I:

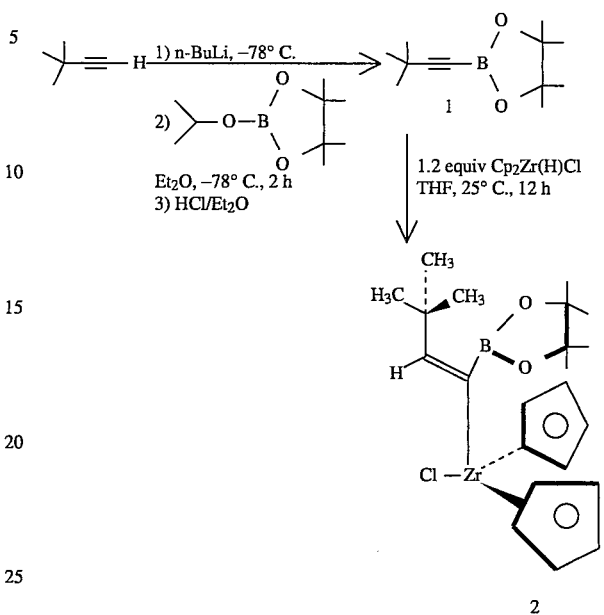

Vinylboronates generally are less reactive than vinylzirconates towards various electrophiles and therefore selective reaction of the latter should be possible. In fact, the reactive nature of compound 2 is illustrated in Scheme II, in which 2 is reacted with several electrophilic reagents. We have found that the selective cleavage of the carbon-zirconium bond in 1,1-bimetalloalkenes by N-halosuccinimides provides (alpha-haloalkenyl)boronic esters in excellent chemical yields and with complete regioselectivity.

Scheme II:

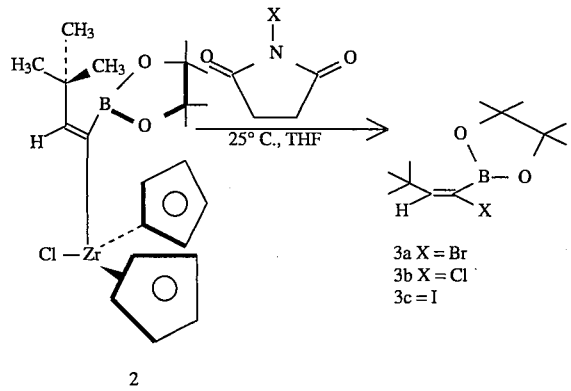

The X-ray analysis of 2 confirmed the configuration of the four-coordinated Zr complex, with two cyclopentadienyl rings Cl and $Csp^2$ as four ligands (FIG. 1). There are two molecules in the asymmetric part of the unit cell. Their configurations are identical, although the conformations differ in details. The mean distances form the central Zr ions to their ligands are as follows: to Cl- 2.520(1)Å, to Csp2- 2.242(4)Å, to Cp1 and Cp2 -2.22(1) Å(where Cp here means the center of the cyclopentadienyl ring). The dihedral angles between the planes defined by Cp1, Zr, Cp2 and Cl Zr, Csp2 are 90° and 89° for molecule A and B respectively. In both molecules the coordination spheres of zirconium form almost regular tetrahedrons. All Cp-rings are planar with ±0.01Å. The tilt angle of 53° is the same in both molecules. However, Cp2 in molecule 2 shows statistical disorder with 60% and 40% occupancies for two observed orientations. The Cp-ring planes corresponding to these positions (C122, 222,322,422,522 and C122A, 222A, 322A, 422A, 522A) make a dihedral angle of 2°. Both heterocyclic rings resemble the typical envelop conformations, with O-B-O-C in the plane and the remaining fifth C atom out of plane (0.46Å and 0.42Å, respectively). Although in molecule A-C3 bends toward metallocene moiety, while in molecule BC15 points outwardly. Also, in molecule A the planar part of the heterocyclic ring makes almost a right angle (86°) with the plane defined by the cis substituted B—C=C—C olefin part of the complex, while in the molecule B the same dihedral angle is only 72°. These two observations are in contrast to the structures of D-mannitol tris(benzeneboronic)ester, two derivatives of streptovaricin C and a derivative of sarcophytol B, where in all cases the boron-containing rings are fairly planar and conjugated with the phenyl rings attached to boron. All bond distances and angles in both molecules agree within the experimental errors and show very good agreement with the values quoted for similar structures. The typical ΠΠ interaction (distance of 3.5Å) is observed between the fragments of Cp1-ring in molecule A (atoms C111 and C511) and Cp2-ring in symmetry related molecule 2 (atoms C522 & 522A, symmetry operation: 1-x, -y, 1-z). The differences in the conformations of the two independent molecules might be related to the packing of molecules in the crystal lattice.

Compound 2 was also unambiguously characterized by $^1H$, $^{11}B$ $^{13}C$-$^1H$ heteronuclear chemical shift correlation NMR spectroscopy. The absence of CB(pp)-Π overlap in solution is indicated by the $^{11}B$ chemical shift ($\delta$=32.3) since this is in the same region ($\delta$=31.1) as the resonance for the corresponding boron-zirconium 1,1-dimetalloalkane, chlorobis (cyclopentadienyl)-[1-( 4,4,5,5-tetramethyl-1,3,2-dioxaborolane-2-yl)- 3,3dimethylbutyl]zirconium (IV). Another interesting feature is the absence of the C-1 (carbon bearing B and Zr) resonance in the $^{13}C$ NMR of a CDCl$_3$ solution. This is attributed to Scalar $^{13}C$ spin-spin relaxation between (i) $^{13}C$ and $^{11}B$, (ii) $^{13}C$ and $^{13}C$ and $^{91}Zr$. Metals with abundant isotopes that have spin quantum numbers exceeding ½ can broaden $^{13}C$ resonances for directly attached (and sometimes remote) carbons in organometallic compounds. In some cases where this scalar spin-spin relaxation occurs, $^{13}C$ signals may not be observed at all, such as for C-1 of 2 in CDCl$_3$. However, in [D$_8$]THF at 25° C., a resonance is visible for C-1 ($\delta$=187.8, W½ht-145 Hz) of 2. Upon lowering the temperature the linewidth of this resonance narrows (W½ht-8 Hz at −95° C.) but its shift is invariant. The magnitude of this shift is outside of the normal range (80 to 145 ppm) for substituted alkenes not bonded to a metal through the alkenyl carbons. Since little difference is found for the $^{13}C$ chemical shifts of non-metallated alkenyl carbons between E and Z isomers, it is instructive to compare these values in 2 ($\delta$(C-1)=187.8, $\delta$(C-2)=120.5,[D$_8$]THF) and E-[1-(4,4,5,5-tetramethyl-1,3, 2-dioxaborolane-2-yl)]-3,3-dimethylbutene ($\delta$(C-1)=112.1, $\delta$(C-2)=164, CDCl$_3$). Here, substitution of H by ZrCp$_2$Cl has deshielded C-1 by 75.7 ppm and shielded C-2 by 41.5 ppm.

The details of the preparation of compounds 1, 2 and 3 are as follows:

1: Compound 1 was prepared according to reference 8. Yield: 11.85 g, 57 mmol, 89%; B.p. 79° C./5 mm Hg; $^1H$ NMR (400 MHz, CDCl$_3$, 25° C., TMS): $\delta$=1.25 (s, 12H, pinacol), $\delta$=1.22 (s, 9H, C(CH$_3$)$_3$); $^{11}B$ NMR (128.3 MHz, CDCl$_3$, 25° C., relative to BF$_3$-Et$_2$O): $\delta$=23.4 (W½ ht =196 Hz).

2: A suspension of Cp$_2$ZrCl(H) (0.51 g, 1.29 mmol) in dry THF (3.8 ml) was stirred at ambient temperature under an atmosphere of argon. 3.3 ml of 0.5M solution of 2-(3,3-dimethylbutynyl)- 4,4,5,5-tetramethyl-1,3,2-dioxaborolane 1 (1.64 mmol) in THF was then added. The reaction mixture was stirred overnight, and became a clear green-yellow solution. After pumping off the THF, hexanes (3×10 ml) was added to extract the reaction mixture. Concentration of the solution and crystallization at −20° C. afforded stable pale green crystals. Yield: 0.55 g, 1.17 mmol, 81.5%.; $^1H$ NMR (400 MHz, CDCl$_3$, 25° C., TMS): $\delta$=6.53 (s,1H, C=CH), 6.08 (s, 10H, Cp), 1.35 (s,12H, pinacol), 1 (s, 9H, C(CH$_3$)$_3$); $^{13}$NMR (100.6 MGz, CDCl$_3$, 25° C., TMS): $\delta$=120.5 (C=CH), 112.2 (Cp), 82.9 (O C(CH$_3$)$_2$), 36.5 (C(CH$_3$)$_3$), 29.5 (C(CH$_3$)$_3$), 25.0 (OC( CH3)2). In CDCl$_3$ solution at 25° C., the C-1 (C bearing B and Zr) resonance was not visible. At 25° C. in [D$_8$]THF, this resonance was observed at $\delta$=1.87.8 (W½ ht=145 Hz). Upon lowering the temperature the shift was invariant but the linewidth decreased (−60° C., W½ ht=14 Hz; −95° C., W½ h=8Hz); $^{11}B$ (128.3 MHz, CDCl$_3$, 25° C., relative to BF$_3$-Et$_2$O): $\delta$=32.3 (W½ ht=518 Hz); CHN analysis: %C=56.68 (calculated=56.65), %H=7.09 (calculated=6.93)

Example 4

This example illustrates the preparation of a stable 1,1-bidentate Lewis Acid based on boron and zirconium.

The synthesis of 2 is outlined in Scheme 1. Treatment of hex-1-yne with HBBr$_2$·Me$_2$S followed by conversion of the dibromoboronic ester to the corresponding alkenylboronic acid and esterification with propane-1,3-diol provided alkenylboronic ester 1. Hydrozirconation of 1 with 3 equiv. of Schwartz's reagent, [Zr(Cp)$_2$(Cl)H], afforded the desired product 2 (86% isolated yield), as a yellow crystalline solid. Compound 2 appears to be stable to dry air in the solid state, but softens and decomposes at 96° C.

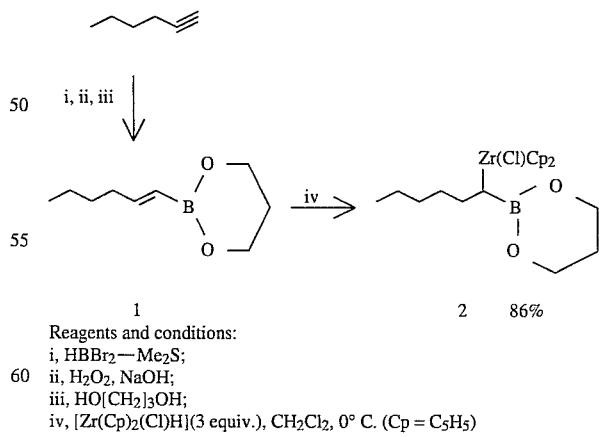

Scheme 1

1        2    86%

Reagents and conditions:
i, HBBr$_2$—Me$_2$S;
ii, H$_2$O$_2$, NaOH;
iii, HO[CH$_2$]$_3$OH;
iv, [Zr(Cp)$_2$(Cl)H](3 equiv.), CH$_2$Cl$_2$, 0° C. (Cp = C$_5$H$_5$)

The X-ray analysis of 2 has proven it to be a complex of four-coordinated Zr with two cyclopentadienyl rings, Cl and the aliphatic C(1) as ligands. There are no intra- or intermolecular interactions between Zr and boron or oxygen atoms. The coordination sphere of zirconium approximates a tetrahedron with a dihedral angle between Cl-Zr-C(1) and Cp(1)-ZR-Cp(2)§ planes being 88.4(1)° ; the dihedral angle between the planes of the cyclopentadienyl rings is 53.0(2)°, both cyclopentadienyl moieties are planar and twisted by 17.7(4) from the fully eclipsed conformation. The distances of Zr to Cp (1) and Cp (2) are 2.205(1) and 2.208(1) Å respectively. The bond length Zr—Cl is 2.459(1)Å and Zr-C(1) is 2.306(4) Å. The conformation of the six-membered heterocyclic ring resembles an envelope with C(9) being 0.619(6) Åout of the plane of the five other atoms.

As indicated in the working Examples, suitable boron-zirconium 1,1-bimetallic compounds have been made and used to produce useful organic materials, the compounds being of the following general structure:

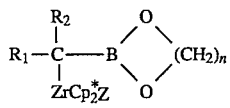

R$_1$ =H, alkyl, aryl
R$_2$ =H, alkyl, aryl
X=O, N—H, N—R, PR$_3$
Y=O, N—H, N—R, PR$_3$
n=1,2,3,4...with various substituents
Z=Cl, Br, I, F.
Cp,*=cyclopentadienyl and any related cyclopentadienyl ligand.

The boron-zirconium dimetallic compounds of the invention are useful in organic synthesis as stoichometric reagents and as Lewis acid catalysts for the polymerization of alpha-olefins.

What is claimed is:

1. An organic bimetallic compound containing Zr and B in which Cp$_2$ is bis(cyclopentadienyl), the compound having the following structure:

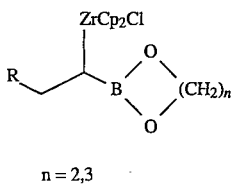

n = 2,3

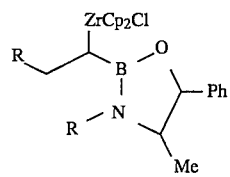

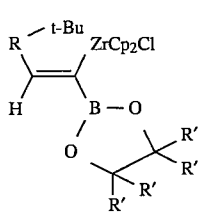

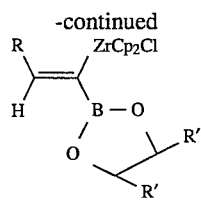

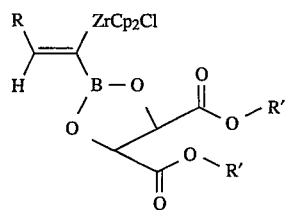

where R is an organic radical having 2 to 20 carbon atoms that is aliphatic, aromatic, heteroaromatic, or cyclic, or their halogenated substituted derivatives; where R$^1$ is an alkyl group of 1 to 8 carbon atoms; where Ph is phenyl, Me is methyl and t-Bu is tert-butyl.

2. A compound as defined in claim 1 in which the structure is:

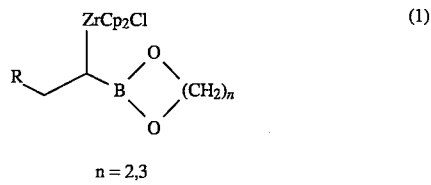

n = 2,3

3. A compound as defined in claim 1 in which the structure is:

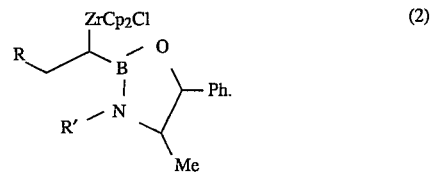

4. A compound as defined in claim 1 in which the structure is:

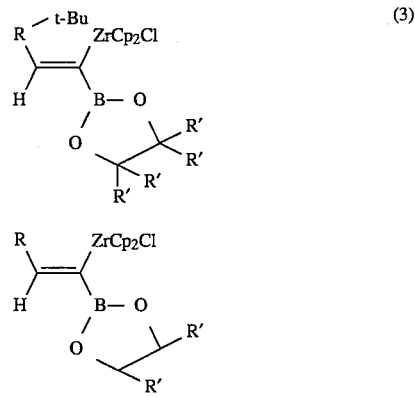

-continued

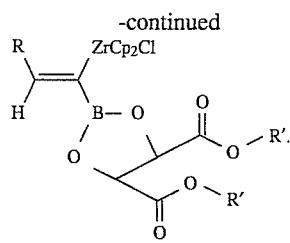

5. A compound as defined in claim 1 in which at least one R radical is tertiary butyl.

6. A compound as defined in claim 1 in which R is methyl, ethyl, propyl, butyl or pentyl.

7. A compound as defined in claim 1 in which R is phenyl, diphenyl, benzyl, or naphthyl.

8. A compound as defined in claim 1 in which R is phenyl propyl, naphthyl propyl, phenyl ethyl or phenyl butyl.

9. A compound as defined in claim 1 in which R is cyclopentyl, cyclohexyl or cyclononyl.

10. A 1,1-bimetallic compound having the following formula:

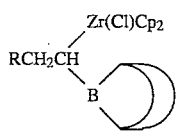

, where R is an alkyl except tert-butyl, alkenyl, cycloalkyl, phenyl, alkyl-phenyl and their chloro- or bromo-substituted derivatives; where

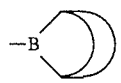

is B-borabicyclo[3.3.1]nonyl, and where $Cp_2$ is bis(cyclopentadienyl).

11. A compound as defined in claim 1 in which R is an alkyl of 1 to 6 carbon atoms.

12. A compound as defined in claim 1 in which R is an alkenyl of 1 to 6 carbon atoms.

13. A 1,1-bimetallic compound having the following formula:

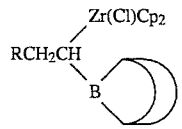

where R is an alkyl except tert-butyl or n-butyl or 1-methylpropyl, alkenyl, cycloalkyl, phenyl, alkyl-phenyl and their chloro- or bromo substituted derivatives; where

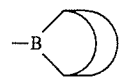

is B-borabicyclo[3.3.1]nonyl, and where $Cp_2$ is bis(cyclopentadienyl).

14. An organic bimetallic compound containing Zr and B in which $Cp_2$ is bis(cyclopentadienyl), the compound having the following structure:

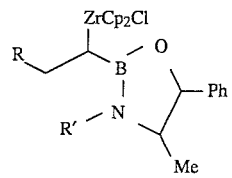

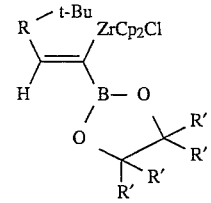

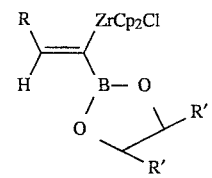

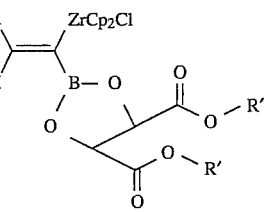

where R is an organic radical having 2 to 20 carbon atoms that is aliphatic, aromatic, heteroaromatic, or cyclic, or their halogenated substituted derivatives; where $R^1$ is an alkyl group of 1 o 8 carbon atoms; where Ph is phenyl, Me is methyl and T-Bu is tert-butyl.

15. A compound as defined in claim 14 in which R is methyl, ethyl, propyl butyl or pentyl.

16. A compound as defined in claim 14 in which R is phenyl, diphenyl, benzyl, or naphthyl.

17. A compound as defined in claim 14 in which R is cyclopentyl, cyclohexyl or cyclononyl.

18. A compound as defined in claim 18 in which the structure is:

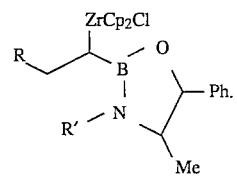

19. A compound as defined in claim 14 in which the structure is:

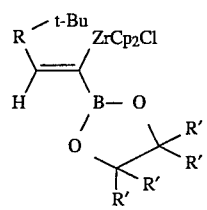
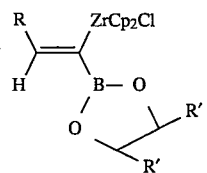
-continued
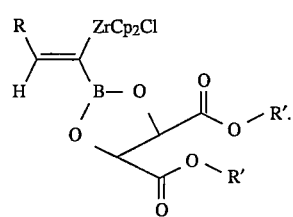
* * * * *